United States Patent
Finn et al.

(10) Patent No.: US 8,703,177 B2
(45) Date of Patent: Apr. 22, 2014

(54) ABUSE-RESISTANT MUCOADHESIVE DEVICES FOR DELIVERY OF BUPRENORPHINE

(75) Inventors: Andrew Finn, Raleigh, NC (US); Niraj Vasisht, Cary, NC (US)

(73) Assignee: BioDelivery Sciences International, Inc., Raleigh, NC (US)

(*) Notice: Subject to any disclaimer, the term of this patent is extended or adjusted under 35 U.S.C. 154(b) by 0 days.

(21) Appl. No.: 13/590,094

(22) Filed: Aug. 20, 2012

(65) Prior Publication Data
US 2013/0045268 A1 Feb. 21, 2013

Related U.S. Application Data

(60) Provisional application No. 61/525,094, filed on Aug. 18, 2011.

(51) Int. Cl.
| | |
|---|---|
| *A61K 9/70* | (2006.01) |
| *A61P 25/00* | (2006.01) |
| *A61P 25/36* | (2006.01) |
| *A61K 31/485* | (2006.01) |

(52) U.S. Cl.
USPC ................. 424/443; 514/279; 514/282

(58) Field of Classification Search
CPC .................. A61K 31/485; A61K 9/006
See application file for complete search history.

(56) References Cited

U.S. PATENT DOCUMENTS

| | | |
|---|---|---|
| 3,640,741 A | 2/1972 | Etes |
| 3,996,934 A | 12/1976 | Zaffaroni |
| 4,226,848 A | 10/1980 | Nagai et al. |
| 4,250,163 A | 2/1981 | Nagai et al. |
| 4,285,934 A | 8/1981 | Tinnell |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,552,751 A | 11/1985 | Inaba et al. |
| 4,572,832 A | 2/1986 | Kigasawa et al. |
| 4,582,835 A | 4/1986 | Lewis et al. |
| 4,594,240 A | 6/1986 | Kawata et al. |
| 4,668,232 A | 5/1987 | Cordes et al. |
| 4,713,243 A | 12/1987 | Schiraldi et al. |
| 4,713,246 A | 12/1987 | Begum et al. |
| 4,715,369 A | 12/1987 | Suzuki et al. |

(Continued)

FOREIGN PATENT DOCUMENTS

| | | |
|---|---|---|
| CA | 2169729 A1 | 2/1995 |
| EP | 0 050 480 A2 | 4/1982 |

(Continued)

OTHER PUBLICATIONS

U.S. Appl. No. 09/069,703, filed Apr. 29, 1998, Tapolsky et al.

(Continued)

*Primary Examiner* — Scott Long
*Assistant Examiner* — Sarah Alawadi
(74) *Attorney, Agent, or Firm* — McCarter & English, LLP; Danielle L. Herritt, Esq.

(57) ABSTRACT

The present invention provides abuse deterrent mucoadhesive devices for delivery of buprenorphine. Each device comprises a mucoadhesive layer and a backing layer, and the pH in each layer is selected, such that absorption of buprenorphine is maximized.

7 Claims, 4 Drawing Sheets

Exemplary Embodiments of the Invention

(56) References Cited

U.S. PATENT DOCUMENTS

| | | |
|---|---|---|
| 4,720,387 A | 1/1988 | Sakamoto et al. |
| 4,740,365 A | 4/1988 | Yukimatsu et al. |
| 4,755,386 A | 7/1988 | Hsiao et al. |
| 4,764,378 A | 8/1988 | Keith et al. |
| 4,765,983 A | 8/1988 | Takayanagi et al. |
| 4,784,858 A | 11/1988 | Ventouras |
| 4,857,336 A | 8/1989 | Khanna et al. |
| 4,867,970 A | 9/1989 | Newsham et al. |
| 4,876,092 A | 10/1989 | Mizobuchi et al. |
| 4,889,720 A | 12/1989 | Konishi |
| 4,894,232 A | 1/1990 | Reul et al. |
| 4,900,552 A | 2/1990 | Sanvordeker et al. |
| 4,900,554 A | 2/1990 | Yanagibashi et al. |
| 4,906,463 A | 3/1990 | Cleary et al. |
| 4,915,948 A | 4/1990 | Gallopo et al. |
| 4,990,339 A | 2/1991 | Scholl et al. |
| 5,047,244 A | 9/1991 | Sanvordeker et al. |
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,149,538 A | 9/1992 | Granger et al. |
| 5,166,233 A | 11/1992 | Kuroya et al. |
| 5,192,802 A | 3/1993 | Rencher |
| 5,196,202 A | 3/1993 | Konishi |
| 5,236,714 A | 8/1993 | Lee et al. |
| 5,254,345 A | 10/1993 | Pogany et al. |
| 5,254,346 A | 10/1993 | Tucker et al. |
| 5,288,497 A | 2/1994 | Stanley et al. |
| 5,298,258 A | 3/1994 | Akemi et al. |
| 5,314,915 A | 5/1994 | Rencher |
| 5,332,576 A | 7/1994 | Mantelle |
| 5,346,701 A | 9/1994 | Heiber et al. |
| 5,462,749 A | 10/1995 | Rencher |
| 5,466,465 A | 11/1995 | Royds et al. |
| 5,505,956 A | 4/1996 | Kim et al. |
| 5,516,523 A | 5/1996 | Heiber et al. |
| 5,540,930 A | 7/1996 | Guy et al. |
| 5,599,554 A | 2/1997 | Majeti |
| 5,603,947 A | 2/1997 | Wong et al. |
| 5,679,714 A | 10/1997 | Weg |
| 5,700,478 A | 12/1997 | Biegajski et al. |
| 5,723,143 A | 3/1998 | Jacques et al. |
| 5,750,136 A | 5/1998 | Scholz et al. |
| 5,780,047 A | 7/1998 | Kamiya et al. |
| 5,800,832 A | 9/1998 | Tapolsky et al. |
| 5,849,322 A | 12/1998 | Ebert et al. |
| 5,853,760 A | 12/1998 | Cremer |
| 5,900,247 A | 5/1999 | Rault et al. |
| 5,948,430 A | 9/1999 | Zerbe et al. |
| 5,985,317 A | 11/1999 | Venkateshwaran et al. |
| 6,159,498 A | 12/2000 | Tapolsky et al. |
| 6,177,096 B1 | 1/2001 | Zerbe et al. |
| 6,200,604 B1 | 3/2001 | Pather et al. |
| 6,228,863 B1 | 5/2001 | Palermo et al. |
| 6,277,384 B1 | 8/2001 | Kaiko et al. |
| 6,284,262 B1 | 9/2001 | Place |
| 6,375,957 B1 | 4/2002 | Kaiko et al. |
| 6,475,494 B2 | 11/2002 | Kaiko et al. |
| 6,562,363 B1 | 5/2003 | Mantelle et al. |
| 6,582,724 B2 | 6/2003 | Hsu et al. |
| 6,592,887 B2 | 7/2003 | Zerbe et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,719,997 B2 | 4/2004 | Hsu et al. |
| 6,759,059 B1 | 7/2004 | Pettersson et al. |
| 6,835,392 B2 | 12/2004 | Hsu et al. |
| 6,969,374 B2 | 11/2005 | Krantz et al. |
| 7,144,587 B2 | 12/2006 | Oshlack et al. |
| 7,157,103 B2 | 1/2007 | Sackler |
| 7,172,767 B2 | 2/2007 | Kaiko et al. |
| 7,579,019 B2 | 8/2009 | Tapolsky et al. |
| 8,147,866 B2 | 4/2012 | Finn et al. |
| 2002/0034554 A1 | 3/2002 | Hsu et al. |
| 2002/0058068 A1 | 5/2002 | Houze et al. |
| 2002/0160043 A1 | 10/2002 | Coleman |
| 2003/0104041 A1 | 6/2003 | Hsu et al. |
| 2003/0124176 A1 | 7/2003 | Hsu et al. |
| 2003/0161870 A1 | 8/2003 | Hsu et al. |
| 2003/0170195 A1 | 9/2003 | Houze et al. |
| 2003/0194420 A1 | 10/2003 | Holl et al. |
| 2004/0018241 A1 | 1/2004 | Houze et al. |
| 2004/0024003 A1 | 2/2004 | Asmussen et al. |
| 2004/0033255 A1 | 2/2004 | Baker et al. |
| 2004/0110781 A1 | 6/2004 | Harmon et al. |
| 2004/0126323 A1 | 7/2004 | Shevchuk et al. |
| 2004/0126416 A1 | 7/2004 | Reidenberg et al. |
| 2004/0151774 A1 | 8/2004 | Pauletti et al. |
| 2004/0191301 A1 | 9/2004 | Van Duren |
| 2004/0213828 A1 | 10/2004 | Smith |
| 2004/0219195 A1 | 11/2004 | Hart et al. |
| 2004/0219196 A1 | 11/2004 | Hart et al. |
| 2004/0220262 A1 | 11/2004 | Hsu et al. |
| 2004/0241218 A1 | 12/2004 | Tavares et al. |
| 2005/0002997 A1 | 1/2005 | Howard et al. |
| 2005/0013845 A1 | 1/2005 | Warren et al. |
| 2005/0042281 A1 | 2/2005 | Singh et al. |
| 2005/0048102 A1 | 3/2005 | Tapolsky et al. |
| 2005/0074487 A1 | 4/2005 | Hsu et al. |
| 2005/0085440 A1 | 4/2005 | Birch et al. |
| 2005/0169977 A1 | 8/2005 | Kanios et al. |
| 2005/0222135 A1 | 10/2005 | Buschmann et al. |
| 2006/0003008 A1 | 1/2006 | Gibson et al. |
| 2006/0069086 A1 | 3/2006 | Michalow |
| 2006/0073102 A1 | 4/2006 | Huaihung et al. |
| 2006/0130828 A1 | 6/2006 | Sexton et al. |
| 2007/0148097 A1 | 6/2007 | Finn et al. |
| 2008/0254105 A1 | 10/2008 | Tapolsky et al. |
| 2009/0270438 A1 | 10/2009 | Booles et al. |
| 2010/0003308 A1 | 1/2010 | Tapolsky et al. |
| 2010/0015183 A1 | 1/2010 | Finn et al. |
| 2010/0168147 A1 | 7/2010 | Chapleo et al. |
| 2011/0033541 A1 | 2/2011 | Myers et al. |
| 2011/0033542 A1 | 2/2011 | Myers et al. |
| 2011/0189259 A1 | 8/2011 | Vasisht et al. |
| 2012/0027839 A1 | 2/2012 | Tapolsky et al. |

FOREIGN PATENT DOCUMENTS

| | | |
|---|---|---|
| EP | 0159604 A2 | 10/1985 |
| EP | 0 250 187 A2 | 12/1987 |
| EP | 0 262 422 A1 | 4/1988 |
| EP | 0 275 550 A1 | 7/1988 |
| EP | 0 381 194 A2 | 8/1990 |
| EP | 0 654 261 A1 | 5/1995 |
| EP | 0 781 546 A1 | 7/1997 |
| EP | 1021204 A2 | 7/2000 |
| EP | 1105104 A1 | 6/2001 |
| EP | 1201233 A1 | 5/2002 |
| FR | 2497098 A1 | 7/1982 |
| FR | 2582942 A1 | 12/1986 |
| GB | 981372 A | 1/1965 |
| GB | 2108841 A | 5/1983 |
| JP | 56-100714 A | 8/1981 |
| JP | 58-079916 A | 5/1983 |
| JP | 60-116630 A | 6/1985 |
| JP | 61-280423 A | 12/1986 |
| JP | 62-022713 A | 1/1987 |
| JP | 62-056420 A | 3/1987 |
| JP | 62-135417 A | 6/1987 |
| JP | 62-178513 A | 8/1987 |
| JP | 63-060924 A | 3/1988 |
| JP | 63-160649 A | 7/1988 |
| JP | 63-310818 A | 12/1988 |
| JP | 64-071812 | 3/1989 |
| JP | 1-226823 A | 9/1989 |
| JP | 3-246220 A | 11/1991 |
| JP | 4-059723 A | 2/1992 |
| JP | 9-504810 | 5/1997 |
| JP | 64-090121 | 4/1999 |
| JP | 2001-508037 A | 6/2001 |

(56) References Cited

FOREIGN PATENT DOCUMENTS

| WO | WO-94/18925 | A1 | | 9/1994 |
|---|---|---|---|---|
| WO | WO-9505416 | A2 | | 2/1995 |
| WO | WO-95/25544 | A1 | | 9/1995 |
| WO | WO-98/26780 | A2 | | 6/1998 |
| WO | WO-01/58447 | A1 | | 8/2001 |
| WO | WO-01/85257 | A2 | | 11/2001 |
| WO | WO-02/92060 | A1 | | 11/2002 |
| WO | WO-03/013525 | A1 | | 2/2003 |
| WO | WO-03/013538 | A1 | | 2/2003 |
| WO | WO-03/070191 | A2 | | 8/2003 |
| WO | WO-2004/017941 | A2 | | 3/2004 |
| WO | WO-2005/044243 | A2 | | 5/2005 |
| WO | WO-2005/055981 | A2 | | 6/2005 |
| WO | WO-2005/081825 | A2 | | 9/2005 |
| WO | WO2008/011194 | | * | 1/2008 |
| WO | WO 2008/100434 | | * | 8/2008 |

OTHER PUBLICATIONS

U.S. Appl. No. 09/684,682, filed Oct. 4, 2000, Tapolsky et al.
U.S. Appl. No. 10/763,063, filed Jan. 22, 2004, Holl et al.
Webster's new World Dictionary (1988), V. Neufeldt ed. and D.B. Guralink ed., Prentice Hall: New York 3rd. College Ed., p. 505.
The Merck Manual, http://www.merck.com/mmhe/sec06/ch078a.html?qt=pain&alt=sh, obtained online on Apr. 9, 2009.
Katz, Nathaniel, P. et al., "Anesthetic and Life Support Drugs Advisory Committee, Meeting, Wednesday, Jan. 2002," retrieved onine at http://www.fda.gov/ohrms/dockets/ac/02/transcripts/3820t1.pdf (2002).
1999 Refresher Course Lecture and Clinical Update Index, retrieved online at http://anesthesia.stanford.edu/RCLS.pdf (1999).
Lahmeyer, H.W. et al., "Pentazocine-naloxone: an 'abuse proof' drug can be abused," *J. Clin. Psychopharmacol.*, vol. 6(6):389-390 (1986).
International Search Report for Appliation No. PCT/US2006/047686, dated Aug. 13, 2007.
McQuinn R.L. et al., "Sustained oral mucosal delivery in human volunteers of buprenorphine from a thin non-eroding mucoadhesive polymeric disk" *Journal of Controlled Release* 34:243-250 (1995).
Guo J.-H. and Cooklock, K.M., "Bioadhesive polymer buccal patches for buprenorphine controlled delivery: solubility consideration" Drug Development and Industrial Pharmacy 21:2013-2019 (1995).
Roy S. et al., "Transdermal delivery of buprenorphine through cadaver skin" Journal of Pharmaceutical Sciences 83:126-130 (1994).
Weinberg, S. et al., "Sublingual absorption of selected opioid analgesics" Clin. Pharmacol. Ther. 44:335-342 (1988).
International Search Report for related PCT Application No. PCT/US2009/048325 dated Aug. 5, 2009.
Written Opinion for related PCT Application No. PCT/US2009/048325 dated Aug. 5, 2009.
International Preliminary Report on Patentability for related PCT Application No. PCT/US2009/048325 dated Jan. 5, 2011.

* cited by examiner

Exemplary Embodiments of the Invention

US 8,703,177 B2

ABUSE-RESISTANT MUCOADHESIVE DEVICES FOR DELIVERY OF BUPRENORPHINE

RELATED APPLICATIONS

This application claims priority to U.S. Provisional Application No. 61/525,094, filed on Aug. 18, 2011. This application is also related to U.S. patent application Ser. No. 08/734,519, filed on Oct. 18, 1996, now U.S. Pat. No. 5,800,832, issued on Sep. 1, 1998; U.S. patent application Ser. No. 11/639,408, filed on Dec. 13, 2006; U.S. patent application Ser. No. 11/817,915, filed on Sep. 6, 2007; and U.S. patent application Ser. No. 13/184,306, filed on Jul. 15, 2011, now U.S. Pat. No. 8,147,866, issued on Apr. 3, 2012. The entire contents of each of the foregoing applications are incorporated herein by reference.

BACKGROUND

Buprenorphine is a partial µ-opiate receptor agonist, an ORL1/nociceptin receptor agonist with high affinity, and slow association and dissociation from the receptors, and a κ-opiate receptor antagonist. Transmucosal bioavailability of buprenorphine is greater than its oral bioavailability, and, as a result, buprenorphine has been initially developed and marketed as a sublingual dosage form. Buprenorphine has been generally available as Temgesic® 0.2 mg sublingual tablets and as Buprenex® in a 0.3 mg/ml parenteral formulation, both indicated for the treatment of moderate to severe pain.

Because there is some risk of abuse with buprenorphine, particularly in the doses used for opioid dependence, a combination product with naloxone, an opioid antagonist, has been developed. The addition of naloxone to buprenorphine decreases the parenteral abuse potential of buprenorphine in opioid dependent subjects, as injected naloxone precipitates withdrawal by displacing the non-buprenorphine opioid from the receptor sites and blocking those sites from buprenorphine occupancy. Human laboratory studies have been conducted to test different dosage ratios of buprenorphine and naloxone (Fudala P. J. et al., Effects of buprenorphine and naloxone in morphine-stabilized opioid addicts, (1998) *Drug Alcohol Depend.*, 50(1):1-8; Mendelson J. et al., Buprenorphine and naloxone combinations: the effects of three dose ratios in morphine-stabilized, opiate-dependent volunteers, (1999) *Psychopharmacology* 141:37-46) and have led to the conclusion that a formulation comprising buprenorphine and naloxone at the dose ratio of w/w 2:1 or 4:1 should be optimal for providing deterrence for opiate abusers. Suboxone® a sublingual pill preparation of buprenorphine that contains buprenorphine and naloxone at a 4:1 w/w dose ratio, and has been approved by the FDA for treating opioid dependence.

SUMMARY OF THE INVENTION

Figure 1:
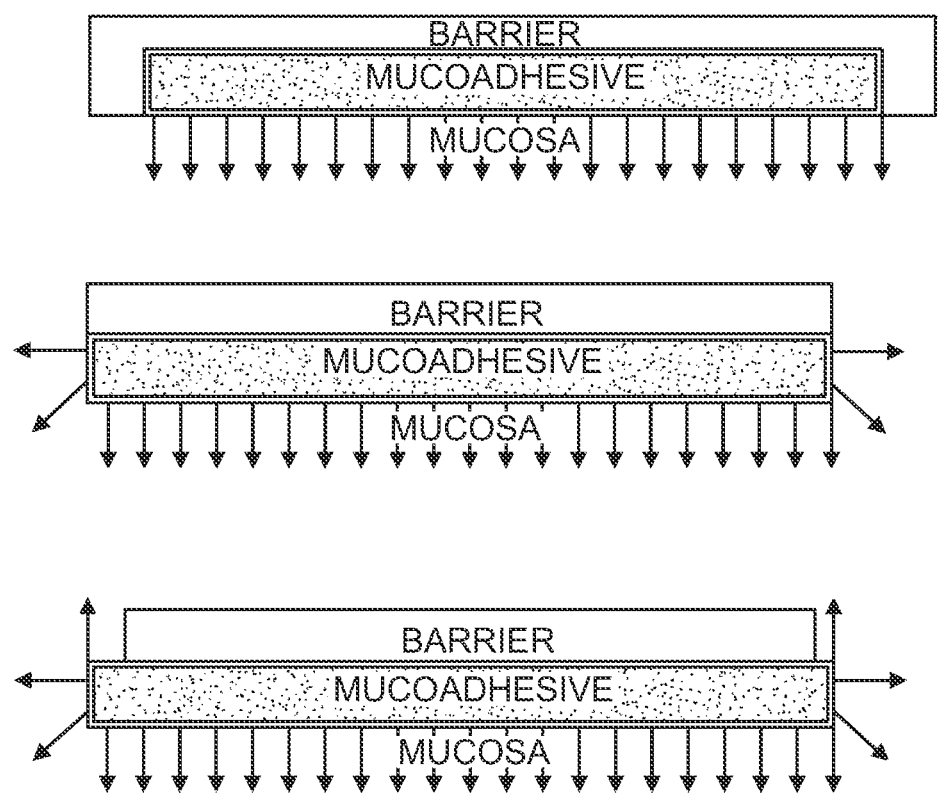
FIG. 1 is a schematic representation of exemplary embodiments of the present invention.

The present invention is based, at least in part, on the discovery that bioavailability of an opioid agonist, e.g., buprenorphine, disposed in the mucoadhesive layer of a two-layered, abuse-resistant transmucosal drug delivery device is not only affected by the pH of the mucoadhesive layer, but is also affected by the pH of the backing layer that resides on the lingual side of the bi-layer film. This layer may or may not contain an opioid antagonist, however in the preferred embodiment of the composition of the backing layer, it does include an opioid antagonist such as naloxone. Accordingly, both the pH of the mucoadhesive layer and the pH of the backing layer may be chosen such that the absorption of buprenorphine from the mucoadhesive layer is similar or higher than absorption from the mucoadhesive layer of a device with an unbuffered backing layer, while the absorption of naloxone, if present in the backing layer, is impeded.

The present invention is also based, at least in part, on the surprising discovery, that the mucoadhesive devices with buffered backing layer may comprise smaller doses of naloxone, while still providing abuse deterrence. The dose of naloxone is lowered, such that the w/w buprenorphine to naloxone ratio is higher than the ratio of 4:1, accepted in the art as being effective for providing abuse deterrence. In some embodiments, the w/w buprenorphine to naloxone ratio present in the mucoadhesive device of the invention is between 4:1 and 10:1. In a specific embodiment, the w/w buprenorphine to naloxone ratio is 6:1. Such a device is advantageous because it can provide effective abuse deterrence at a lower naloxone dose.

This invention does not purport the need for naloxone in the backing layer. In some embodiments, the amount of naloxone required to precipitate withdrawal is as low as 0.1 mg when abused by injection. In some embodiments, the maximum ratio of buprenorphine dose to naloxone is 10:1 and can be as low at 1:1. In some embodiments, the ratio of buprenorphine dose to naloxone is 10:1 to 4:1. In a specific embodiment, the ratio is 6:1.

In some embodiments, the present invention provides an abuse deterrent mucoadhesive device for use in managing pain or opioid dependence, the device comprising:
a mucoadhesive layer comprising buprenorphine buffered to a pH of between about 4.0 and about 6.0; and
a backing layer buffered to a pH between about 4.0 and about 4.8.

In some embodiments, the absorption of buprenorphine through the oral mucosal membrane is optimized and a therapeutically effective dose of buprenorphine is provided. In some embodiments, the backing layer comprises naloxone. In some embodiments, the w/w ratio of buprenorphine to naloxone present in the device is between 1:1 and 10:1. In some embodiments, the ratio is between about 4:1 and 10:1. In a preferred embodiment, the w/w ratio of buprenorphine to naloxone present in the device is 6:1.

In some embodiments, the present invention provides an abuse deterrent mucoadhesive device for use in managing pain or opioid dependence, the device comprising:

a mucoadhesive layer comprising buprenorphine buffered to a pH of between about 4.0 and about 6.0;
and a backing layer buffered to a pH between about 4.0 and about 4.8;
wherein bioavailability of buprenorphine absorbed from the device is greater than 40%. In some embodiments, the bioavailability is about 60%. In some embodiments, the bioavailability is about 65%. In some embodiments, the bioavailability is about 75%.

In some embodiments, the mucoadhesive layer is buffered to a pH of between about 4.50 and about 5.50 and the backing layer is buffered to a pH of between about 4.10 and about 4.4. In a preferred embodiment, the mucoadhesive layer is buffered to a pH of about 4.75 and the backing layer is buffered to a pH of about 4.25.

In some embodiments, the device comprises about 0.075-12 mg of buprenorphine. In some embodiments, the amount of buprenorphine is 0.15-12 mg of buprenorphine. In some embodiments, the device also comprises about 0.0125-2 mg of naloxone. In some embodiments, the amount of naloxone is about 0.1-2 mg. In some embodiments, the bioavailability of buprenorphine absorbed from the device is greater than 40%.

In some embodiments, the present invention provides an abuse deterrent mucoadhesive device for use in managing pain or opioid dependence, the device comprising:
a mucoadhesive layer comprising buprenorphine and buffered to a first pH;
a backing layer buffered to a second pH;
the second pH selected such that the transmucosal delivery of buprenorphine is not impeded, such that the bioavailability of buprenophine is greater than 40%. In some embodiments, the backing layer comprises naloxone, and the delivery of naloxone is impeded.

In some embodiments, the invention also provides an abuse deterrent mucoadhesive device for use in managing pain or opioid dependence, the device comprising:
a mucoadhesive layer comprising buprenorphine and buffered to a first pH,
a backing layer buffered to a second pH,
the first pH and the second pH selected such that the unidirectional delivery gradient of buprenorphine toward the mucosa is not impeded, such that the total bioavailability of buprenophine provided by the device is similar to the total bioavailability of buprenorphine provided by the same device wherein the pH of the backing layer is not adjusted. In one embodiment, the backing layer comprises naloxone, and the delivery of naloxone is impeded.

In some embodiments, an abuse deterrent mucoadhesive device for use in managing pain or opioid dependence comprises:
a mucoadhesive layer comprising buprenorphine and buffered to a first pH and a backing layer buffered to a second pH;
wherein the first pH is between about 4.0 and about 6.0;
wherein the second pH is between about 4.0 and about 4.8.
In some embodiments, the backing layer comprises naloxone. In some embodiments, buprenorphine and naloxone disposed in the device are present in w/w ratio of about 4:1 to about 10:1 of buprenorphine:naloxone. In one embodiment, the ratio is about 6:1.
In some embodiments, the first pH is between about 4.50 and about 5.50 and the second pH is between about 4.10 and about 4.4. In a specific embodiment, the first pH is about 4.75 and the second pH is about 4.25. In some embodiments, the device comprises about 0.075 to 12 mg of buprenorphine and about 0.0125-2 mg of naloxone.

In some embodiments, an abuse deterrent mucoadhesive device for use in managing pain or opioid dependence comprises:
a mucoadhesive layer comprising buprenorphine and buffered to a first pH and a backing layer buffered to a second pH;
wherein the first pH is between about 4.0 and about 6.0;
wherein the second pH is between about 4.0 and about 4.8; and
wherein bioavailability of buprenorphine absorbed from the device is greater than 40%. In some embodiments, the backing layer comprises naloxone.

In some embodiments, the first pH is between about 4.50 and about 5.50 and the second pH is between about 4.10 and about 4.4. In a specific embodiment, the first pH is about 4.75 and the second pH is about 4.25. In some embodiments, the device comprises about 0.075 to 12 mg of buprenorphine and about 0.0125-2 mg of naloxone.

In a preferred embodiment, the abuse deterrent mucoadhesive device for use in managing pain or opioid dependence comprises:
a mucoadhesive layer comprising buprenorphine and buffered to a first pH and a backing layer comprising naloxone and buffered to a second pH;
wherein the first pH is about 4.75;
wherein the second pH is about 4.25; and
wherein buprenorphine and naloxone disposed in the device are present in w/w ratio of about 6:1 of buprenorphine:naloxone.

In some embodiments, methods of treating pain or managing opioid dependence in a subject are also provided. The methods generally comprise administering to a subject in need thereof an abuse deterrent mucoadhesive device of the invention, such that pain is treated or opioid dependence is managed in a subject.

DETAILED DESCRIPTION OF THE INVENTION

Definitions

The following definitions are provided as guidance as to the meaning of certain terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

As used herein, the term "absorption" refers to the process of a substance, such as a drug, entering the bloodstream. Absorption can be measured by pharmacokinetic parameters, such as $AUC_{inf}$ and $C_{max}$.

As used herein, the term "acute pain" refers to pain characterized by a short duration, e.g., three to six months. Acute pain is typically associated with tissue damage, and manifests in ways that can be easily described and observed. It can, for example, cause sweating or increased heart rate. Acute pain can also increase over time, and/or occur intermittently.

As used herein, the term "bioavailability" is as defined in 21 CFR Section 320.1 and refers to the rate and extent to which the active ingredient or active moiety is absorbed from a drug product and becomes available at the site of action. The term "bioavailable," "absolute bioavailability" or "total bioavailability" refers to the total bioavailability including amounts that are transmitted via the mucosal membrane (i.e., transmucosally) and through the GI tract. The term "absolute bioavailability" refers to a fraction of a drug absorbed through non-intravenous administration (i.e., transmucosal, oral, rectal, transdermal, subcutaneous, or sublingual administration) compared with the bioavailability of the same drug following intravenous administration. The comparison is dose normalized, i.e., accounts for different doses consequently, the amount absorbed is corrected by dividing the corresponding dose administered. In some embodiments, the mucoadhesive devices of the present invention provide absolute bioavailability of the opioid agonist buprenorphine that is equal to or greater than 40%, e.g., 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

As used herein, the term "bioequivalence" or "bioequivalent" is as defined in 21 CFR Section 320.1, and means the absence of a significant difference in the rate and extent of absorption of an active ingredient or active moiety in one pharmaceutical product and another. For bioequivalence, the pharmacokinetic parameters $C_{max}$ and AUC for bioequivalent actives fall within the 80%-125% range of each other. In some embodiments, the devices of the present invention may be bioequivalent to Suboxone® sublingual tablet. Pharmacokinetic parameters, e.g., $C_{max}$ and $AUC_{inf}$, for Suboxone® sublingual tablets comprising 2.0/0.5 mg and 8.0/2.0 mg of buprenorphine/naloxone is contained in the product label for Suboxone®, which is incorporated herein by reference in its entirety.

As used herein, the term "chronic pain" refers to pain which persists beyond the usual recovery period for an injury or illness. Chronic pain can be constant or intermittent. Common causes of chronic pain include, but are not limited to, arthritis, cancer, Reflex Sympathetic Dystrophy Syndrome (RSDS), repetitive stress injuries, shingles, headaches, fibromyalgia, and diabetic neuropathy, lower back pain, neck and shoulder pain, moderate to severe osteoarthritis, and patients with severe migraine.

As used herein, unless indicated otherwise, the term "buprenorphine", includes any pharmaceutically acceptable form of buprenorphine, including, but not limited to, salts, esters, and prodrugs thereof. In one embodiment, the term "buprenorphine" refers to buprenorphine hydrochloride. As used herein, the term "buprenorphine derivative" refers to compounds having similar structure and function to buprenorphine. In some embodiments, buprenorphine derivatives include those of the following formula:

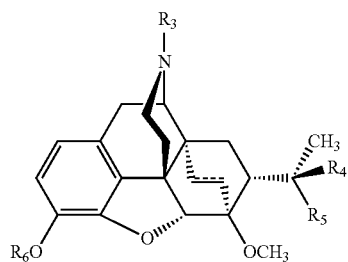

or pharmaceutically acceptable salts or esters thereof, wherein

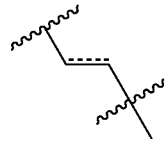

is a double or single bond; $R_3$ is selected from a —$C_{1-4}$ alkyl group or a cycloalkyl-substituted-$C_{1-4}$ alkyl group; $R_4$ is selected from a —$C_{1-4}$ alkyl; $R_5$ is —OH, or taken together, $R_4$ and $R_5$ form a =O group; and $R_6$ is selected from —H or a —$C_{1-4}$ alkyl group.

Buprenorphine derivatives include, but are not limited to, etorphine and diprenorphine. General buprenorphine derivatives are described in WO 2008/011194, which is hereby incorporated by reference.

As used herein, unless indicated otherwise, the term "naloxone" includes any pharmaceutically acceptable form of naloxone, including, but not limited to, salts, esters, and prodrugs thereof. In one embodiment, the term "naloxone" refers to naloxone hydrochloride. In some embodiments, naloxone is represented by the following chemical structure:

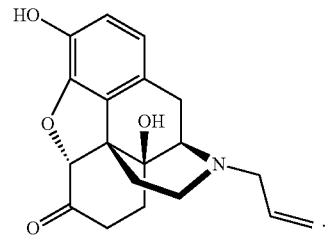

As used herein, the term "mucoadhesive layer" or "polymeric diffusion environment" refers to an environment capable of allowing flux of a medicament to a mucosal surface upon creation of a gradient by adhesion of the polymeric diffusion environment to a mucosal surface. The flux of a transported medicament is proportionally related to the diffusivity of the environment which can be manipulated by, e.g., adjusting the pH, taking into account the ionic nature of the medicament and/or the ionic nature of the polymer or polymers included in the environment.

As used herein, the term "backing layer" or "non-adhesive polymeric environment" refers to an environment in the form of, e.g., a layer or coating or barrier layer, capable of slowing, reducing or stopping flux of a medicament in its direction and does not adhere to surfaces in the oral cavity. In some embodiments, the pH of the backing layer is adjusted, such as it stops flux of a medicament contained therein and in the mucoadhesive layer, except in the direction of the mucosa. In some embodiments, the non-adhesive polymeric environment significantly slows flux of a medicament, e.g., enough so that little or no medicament is washed away by saliva. In some embodiments, the non-adhesive polymeric environment slows or stops flux of a medicament, while allowing hydration of the polymeric diffusion environment e.g., by saliva.

As used herein, the term "unidirectional gradient" refers to a gradient which allows for the flux of a medicament (e.g., buprenorphine) through the device, e.g., through a polymeric diffusion environment, in substantially one direction, e.g., to the mucosa of a subject. For example, the polymeric diffusion environment may be a mucoadhesive polymeric diffusion environment in the form of a layer or film disposed adjacent to a backing layer or film. Upon mucosal administration, a gradient is created between the mucoadhesive polymeric diffusion environment and the mucosa, and the medicament flows from the mucoadhesive polymeric diffusion environment, substantially in one direction towards the mucosa. In some embodiments, some flux of the medicament is not entirely unidirectional across the gradient; however, there is typically not free flux of the medicament in all directions.

As used herein, "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder (e.g., to alleviate pain).

The term "subject" refers to living organisms such as humans, dogs, cats, and other mammals. Administration of the medicaments included in the devices of the present invention can be carried out at dosages and for periods of time effective for treatment of a subject. In some embodiments, the subject is a human. In some embodiments, the pharmacokinetic profiles of the devices of the present invention are similar for male and female subjects.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

The term "transmucosal," as used herein, refers to any route of administration via a mucosal membrane. Examples include, but are not limited to, buccal, sublingual, nasal, vaginal, and rectal. In one embodiment, the administration is buccal. In one embodiment, the administration is sublingual. As used herein, the term "direct transmucosal" refers to mucosal administration via the oral mucosa, e.g., buccal and/or sublingual.

As used herein, the term "water erodable" or "at least partially water erodable" refers to a substance that exhibits a water erodability ranging from negligible to completely water erodable. The substance may readily dissolve in water or may only partially dissolve in water with difficulty over a long period of time. Furthermore, the substance may exhibit a differing erodability in body fluids compared with water because of the more complex nature of body fluids. For example, a substance that is negligibly erodable in water may show an erodability in body fluids that is slight to moderate. However, in other instances, the erodability in water and body fluid may be approximately the same.

The term "impeded" when used to describe the absorption or the delivery of the opioid antagonist from the abuse-resistant device refers to the absorption and/or delivery of said opioid antagonist that is insufficient to inhibit the effects of the opioid agonist comprised in the same device.

As used herein, "addiction therapy" as related to a subject includes the administration of a drug to a subject with the purpose of reducing the cravings for the addictive substance.

As used herein, the term "abusive" or "abusive manner" refers to uses of the devices beyond transmucosal administration such as by injecting or snorting.

As used herein, the term "disposed" refers to the uniform or non-uniform distribution of an element within another.

Maintenance Treatment of Opioid Dependence

Certain aspects of the present invention include methods for providing maintenance treatment for a subject addicted to opioids. Presently, buprenorphine maintenance is one of the most promising courses of action for addicted subjects in terms of long-term abstinence.

Pain Management

Certain aspects of the present invention include methods for providing pain management and/or relief to a subject in need thereof. The pain can be any pain known in the art, caused by any disease, disorder, condition and/or circumstance and can be chronic pain or acute pain.

Transmucosal Mucoadhesive Pharmaceutical Delivery Device

In certain aspects of the present invention, abuse-resistant transmucosal delivery devices are provided. Accordingly, in one embodiment, the present invention is directed to abuse-resistant mucoadhesive delivery devices suitable for administration of an effective amount of an opioid drug to a subject, for the management of pain and/or opioid dependence. The device is capable of delivering the opioid agonist by means of a unidirectional gradient (i.e. flux that flows toward the mucosa) that is created upon application of the device to a mucosal surface.

The devices of the present invention can include any combination or sub-combination of ingredients, layers and/or compositions of, e.g., the devices described in U.S. Pat. Nos. 6,159,498, 5,800,832, 6,585,997, 6,200,604, 6,759,059 and/or PCT Publication No. WO 05/06321. The contents of these patent and publications are incorporated herein by reference in their entireties.

i. Mucoadhesive Layer

In some embodiments, the mucoadhesive layer is a bioerodable or water-erodable mucoadhesive layer. In some embodiments, the devices of the present invention include a bioerodable mucoadhesive layer which comprises a mucoadhesive polymeric diffusion environment. The device adheres to a mucosal surface of the subject within about 5 seconds following application.

In some embodiments, the mucoadhesive polymeric diffusion environment comprises an opioid agonist. In some embodiments, the opioid agonist is buprenorphine. In some embodiments related to the treatment of opioid dependence, the dose of buprenorphine that can be incorporated into the device of the present invention depends on the desired treatment dosage to be administered and can range from about 10 µg to about 20 mg of buprenorphine. In other embodiments related to the treatment of pain, the dose of buprenorphine can range from about 60 µg to about 6 mg. In some embodiments, the low dose of buprenorphine comprised in the mucoadhesive device of the invention is between about 0.075 and 12 mg of buprenorphine, e.g., 0.075 mg, 0.080 mg, 0.085 mg, 0.090 mg, 0.095 mg, 0.10 mg, 0.15 mg, 0.20 mg, 0.25 mg, 0.30 mg, 0.35 mg, 0.40 mg, 0.45 mg, 0.50 mg, 0.44 mg, 0.60 mg, 0.65 mg, 0.70 mg, 0.75 mg, 0.80 mg, 0.85 mg, 0.90 mg, 0.95 mg, 1.00 mg, 1.5 mg, 1.75 mg, 2.0 mg, 2.5 mg, 3.0 mg, 3.5 mg, 4.0 mg, 4.5 mg, 5.0 mg, 5.25 mg, 5.5 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.5 mg or 12.0 mg or buprenorphine. In one embodiment, the dose is 0.875 mg of buprenorphine. In another embodiment, the dose is 1.75 mg of buprenorphine. In another embodiment, the dose is 3.5 mg of buprenorphine. In yet another embodiment, the dose is 5.25 mg of buprenorphine.

In some embodiments, the mucoadhesive polymeric diffusion environment can include the drug, at least one pharmacologically acceptable polymer capable of bioadhesion (the "bioadhesive polymer"), and can optionally include at least one film-forming bioerodable or water-erodable polymer (the "film-forming polymer"). Alternatively, the mucoadhesive polymeric diffusion environment can be formed of a single polymer that acts as both the bioadhesive polymer and the first film-forming polymer. Additionally or alternatively, the mucoadhesive polymeric diffusion environment can include other film-forming water-erodable polymers and/or water-erodable plasticizers, such as glycerin and/or polyethylene glycol (PEG).

In some embodiments, the bioadhesive polymer of the mucoadhesive polymeric diffusion environment can include any water erodable substituted cellulosic polymer or substituted olefinic polymer wherein the substituents may be ionic or hydrogen bonding, such as carboxylic acid groups, hydroxyl alkyl groups, amine groups and amide groups. For hydroxyl containing cellulosic polymers, a combination of alkyl and hydroxyalkyl groups will be preferred for provision of the bioadhesive character and the ratio of these two groups will have an effect upon water swellability and dispersability. Examples include polyacrylic acid (PAA), which can optionally be partially cross-linked, sodium carboxymethyl cellulose (NaCMC), moderately to highly substituted hydroxypropylmethyl cellulose (HPMC), polyvinylpyrrolidone (PVP3 which can optionally be partially cross-linked), moderately to highly substituted hydroxyethylmethyl cellulose (HEMC) or combinations thereof. In one embodiment, HEMC can be used as the bioadhesive polymer and the first film forming polymer as described above for a mucoadhesive polymeric diffusion environment formed of one polymer. These bioadhesive polymers are preferred because they have good and instantaneous mucoadhesive properties in a dry, system state.

In some embodiments, the mucoadhesive polymeric diffusion environment, e.g., a bioerodable mucoadhesive layer, is generally comprised of water-erodable polymers which include, but are not limited to, hydroxyethyl cellulose (HEC), hydroxypropyl cellulose (HPC), hydroxypropylmethyl cellulose (HPMC), hydroxyethylmethyl cellulose (HEMC), polyacrylic acid (PAA) which may or may not be partially cross-linked, sodium carboxymethyl cellulose (NaCMC), and polyvinylpyrrolidone (PVP), or combinations thereof. Other mucoadhesive water-erodable polymers may also be used in the present invention. The term "polyacrylic acid" includes both uncross-linked and partially cross-linked forms, e.g., polycarbophil.

Similar film-forming water-erodable polymers can also be used. The film-forming water-erodable polymers can optionally be cross-linked and/or plasticized in order to alter its dissolution kinetics.

In some embodiments, the properties of the mucoadhesive polymeric diffusion environment are influenced by its pH. In some embodiments, e.g., when mucoadhesive polymeric diffusion environment comprises buprenorphine, its pH is between about 4.0 and about 7.5. In one embodiment, the pH is between 4.0 and 6.0, more specifically, between 4.5 and 5.5, and even more specifically, between 4.75 and 5.25. In a specific embodiment, the pH is 4.75. It is to be understood that all values and ranges between these values and ranges are meant to be encompassed by the present invention.

The pH of the mucoadhesive polymeric diffusion environment can be adjusted and/or maintained by methods including, but not limited to, the use of buffering agents, or by adjusting the composition of the device of the present invention.

Buffering agents suitable for use with the present invention include, for example, phosphates, such as sodium phosphate; phosphates monobasic, such as sodium dihydrogen phosphate and potassium dihydrogen phosphate; phosphates dibasic, such as disodium hydrogen phosphate and dipotassium hydrogen phosphate; phosphates tribasic, such as trisodium phosphate; citrates, such as sodium citrate (anhydrous or dehydrate) and triethyl citrate; bicarbonates, such as sodium bicarbonate and potassium bicarbonate; acetates, such as sodium acetate, may be used. In one embodiment, a single buffering agent, e.g., a dibasic buffering agent is used. In another embodiment, a combination of buffering agents is employed, e.g., a combination of a tri-basic buffering agent and a monobasic buffering agent. In some embodiments, the amount of buffering agent is present in a composition used to make the mucoadhesive layer is about 1 to 20% of the amount of the agonist drug, e.g., buprenorphine.

ii. Backing Layer

The device further comprises at least one additional non-adhesive polymeric environment, e.g., a backing layer. This layer is disposed adjacent to the mucoadhesive polymeric diffusion environment, e.g., a backing layer, functions to facilitate the delivery of the opioid agonist, such as buprenorphine, to the mucosa. This additional layer may comprise the same or a different combination of polymers as the mucoadhesive polymeric diffusion environment or the non-adhesive polymeric diffusion environment.

In some embodiments, the backing layer includes an additional medicament, such as an opioid antagonist, to render the device of the invention abuse-resistant. In some embodiments, the opioid antagonist is naloxone. The dose of naloxone that can be incorporated into the device of the present invention depends on the desired treatment dosage to be administered and can range from about 100 µg to 5 mg of naloxone for the treatment of dependence, and from 60 µg to 1.5 mg naloxone for the pain indication. In some embodiments, the dose of naloxone is between about 0.0125 mg to about 2.0 mg of naloxone, e.g., 0.0125 mg, 0.0130 mg, 0.0135 mg, 0.0140 mg, 0.0145 mg, 0.0150 mg, 0.0155 mg, 0.0160 mg, 0.0165 mg, 0.0170 mg, 0.0175 mg, 0.0180 mg, 0.0185 mg, 0.0190 mg, 0.0195 mg, 0.02 mg, 0.03 mg, 0.04 mg, 0.05 mg, 0.06 mg, 0.07 mg, 0.08 mg, 0.09 mg, 0.1 mg, 0.145 mg, 0.2 mg, 0.29 mg, 0.3 mg, 0.4 mg, 0.5 mg, 0.58 mg, 0.6 mg, 0.7 mg, 0.8 mg, 0.87 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg or 2.0 mg of naloxone. In one embodiment, the dose is 0.145 mg of naloxone. In another embodiment, the dose is 290 µg of naloxone. In another embodiment, the dose is 580 µg of naloxone. In yet another embodiment, the dose is 870 µg of naloxone. In some embodiments, the amount of buprenorphine and the amount of naloxone disposed in the device are present in a ratio chosen such that the effect of buprenorphine is negated by naloxone if the mixture is injected or snorted. In such embodiment, buprenorphine and naloxone disposed in the device are present in a w/w ratio that ranges between 1:4 and 1:10. In a preferred embodiment, the w/w ratio of buprenorphine to naloxone is 1:4 to 1:6, wherein 1:6 is the most preferred embodiment.

In some embodiments, the backing layer (i.e., the non-adhesive polymeric embodiment) functions as a barrier to facilitate a unidirectional flux of the medicament, e.g., buprenorphine, disposed in the mucoadhesive layer. Upon application to a mucosal surface, a diffusional gradient of a medicament is created towards the mucosa. In another embodiment the backing layer, can serve an erodible polymer that facilitate absorption of buprenorphine in the orophyrangeal tissue. In some embodiments, prevents diffusion away from the mucosal surface. In such instances, a majority of the medicament, i.e., at least 50% flows towards the mucosa. In other embodiments, as depicted in FIG. 1, the non-adhesive polymeric environment may circumscribe the boundaries of the mucoadhesive polymeric diffusion environment thereby ensuring that medicament flows toward the mucosa.

The backing layer (e.g., a water-erodable non-adhesive backing layer) can further include at least one water erodable, film-forming polymer. This layer may optionally include a drug. The polymer or polymers can include polyethers and polyalcohols as well as hydrogen bonding cellulosic polymers having either hydroxyalkyl group substitution or hydroxyalkyl group and alkyl group substitution preferably with a moderate to high ratio of hydroxyalkyl to alkyl group. Examples include, but are not limited to, hydroxyethyl cellulose (HEC), hydroxypropyl cellulose (HPC), hydroxypropylmethyl cellulose (HPMC), hydroxyethylmethyl cellulose (HEMC), polyvinyl alcohol (PVA), polyethylene glycol (PEG), polyethylene oxide (PEO), ethylene oxide-propylene oxide co polymers, ethylene oxide-propylene oxide co-polymers, and combinations thereof. The water-erodable non-adhesive backing layer component can optionally be crosslinked.

In certain embodiments, the non-adhesive backing layer is free of cross-linked polymers. In a preferred embodiment of the device, the non-adhesive backing layer is free of polyacrylic acid. While not wishing to be bound by any specific theory, it is estimated that the residence time is reduced by the absence of said polyacrylic acid. For example, in certain embodiments, the residence time is between 15 and 30 minutes. In a preferred embodiment, the water erodable non-adhesive backing layer includes hydroxyethyl cellulose and hydroxypropyl cellulose.

The devices of the present invention can include ingredients that are employed to, at least in part, provide a desired residence time. In some embodiments, this is a result of the selection of the appropriate backing layer formulation, providing a slower rate of erosion of the backing layer. Thus, the non-adhesive backing layer is further modified to render controlled erodability which can be accomplished by coating the backing layer film with a more hydrophobic polymer selected from a group of FDA approved Eudragit™ polymers, ethyl cellulose, cellulose acetate phthalate, and hydroxyl propyl methyl cellulose phthalate, that are approved for use in other pharmaceutical dosage forms. Other hydrophobic polymers may be used, alone or in combination with other hydrophobic or hydrophilic polymers, provided that the layer derived from these polymers or combination of polymers erodes in a moist environment. Dissolution characteristics may be adjusted to modify the residence time and the release profile of a drug when included in the backing layer.

In some embodiments, any of the layers in the devices of the present invention may also contain a plasticizing agent, such as propylene glycol, polyethylene glycol, or glycerin in a small amount, 0 to 15% by weight, in order to improve the "flexibility" of this layer in the mouth and to adjust the erosion rate of the device. In addition, humectants such as hyaluronic acid, glycolic acid, and other alpha hydroxyl acids can also be added to improve the "softness" and "feel" of the device. Finally, colors and opacifiers may be added to help distinguish the resulting non-adhesive backing layer from the mucoadhesive polymeric diffusion environment. Some opacifers include titanium dioxide, zinc oxide, zirconium silicate, etc.

The device can also optionally include a pharmaceutically acceptable dissolution-rate-modifying agent, a pharmaceutically acceptable disintegration aid (e.g., polyethylene glycol, dextran, polycarbophil, carboxymethyl cellulose, or poloxamers), a pharmaceutically acceptable plasticizer, a pharmaceutically acceptable coloring agent (e.g., FD&C Blue #1), a pharmaceutically acceptable opacifier (e.g., titanium dioxide), pharmaceutically acceptable anti-oxidant (e.g., tocopherol acetate), a pharmaceutically acceptable system forming enhancer (e.g., polyvinyl alcohol or polyvinyl pyrrolidone), a pharmaceutically acceptable preservative, flavorants (e.g., saccharin and peppermint), neutralizing agents (e.g., sodium hydroxide), buffering agents (e.g., monobasic, or tribasic sodium phosphate), or combinations thereof. Preferably, these components are individually present at no more than about 1% of the final weight of the device, but the amount may vary depending on the other components of the device.

In some embodiments, the non-adhesive polymeric diffusion environment, e.g., the backing layer, is a buffered environment. In some embodiments the pH of the backing layer is between 4.0 and 6.0, more specifically, between 4.2 and 4.7, and even more specifically, between 4.2 and 4.4. In one embodiment, the pH of the backing layer is 4.25. It is to be understood that all values and ranges between these values and ranges are meant to be encompassed by the present invention.

The pH of the backing layer can be adjusted and/or maintained by methods including, but not limited to, the use of buffering agents, or by adjusting the composition of the device of the present invention. In some embodiments, the properties of the polymeric diffusion environment are influenced by its buffering capacity. In some embodiments, buffering agents are included in the mucoadhesive polymeric diffusion environment. Buffering agents suitable for use with the present invention include, for example, phosphates, such as sodium phosphate; phosphates monobasic, such as sodium dihydrogen phosphate and potassium dihydrogen phosphate; phosphates dibasic, such as disodium hydrogen phosphate and dipotassium hydrogen phosphate; phosphates tribasic, such as trisodium phosphate; citrates, such as sodium citrate (anhydrous or dehydrate) and triethyl citrate; bicarbonates, such as sodium bicarbonate and potassium bicarbonate; acetates, such as sodium acetate, may be used. In one embodiment, a single buffering agent, e.g., a dibasic buffering agent is used. In another embodiment, a combination of buffering agents is employed, e.g., a combination of a tri-basic buffering agent and a monobasic buffering agent. In some embodiments, the backing layer comprises the opioid antagonist. In another embodiment, the backing layer comprises an opioid antagonist that is present as a microencapsulated particle with polymers. These polymers include, but are not limited to alginates, polyethylene oxide, poly ethylene glycols, polylactide, polyglycolide, lactide-glycolide copolymers, poly-epsilon-caprolactone, polyorthoesters, polyanhydrides and derivatives, methyl cellulose, ethyl cellulose, hydroxypropyl cellulose, hydroxyethyl cellulose, hydroxyethylmethyl cellulose, hydroxypropylmethyl cellulose, polyacrylic acid, and sodium carboxymethyl cellulose, poly vinyl acetate, poly vinyl alcohols, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin, chitosan bioadhesive polymers, polyacrylic acid, polyvinyl pyrrolidone, sodium carboxymethyl cellulose and combinations thereof.

EXEMPLIFICATION OF THE INVENTION

The invention will be further understood by the following examples. However, those skilled in the art will readily appreciate that the specific experimental details are only illustrative and are not meant to limit the invention as described herein, which is defined by the claims which follow thereafter.

Example 1

Preparation of the Devices of the Invention

Several formulations were prepared comprising different doses of buprenorphine and naloxone, with the backing layers adjusted to different pHs, as described in the Table 1 below:

TABLE 1

Formulations of the invention

| Formulation No. | pH backing layer | pH mucoadhesive layer | Buprenorphine (mg) | Naloxone (mg) | Ratio of buprenorphine to naloxone (w/w) |
|---|---|---|---|---|---|
| 1 | 2.8 | 4.75 | 0.75 | 0.1875 | 4:1 |
| 2 | 2.8 | 4.75 | 3.0 | 0.75 | 4:1 |
| 3 | 4.25 | 4.75 | 0.75 | 0.1875 | 4:1 |
| 4 | 4.25 | 4.75 | 3.0 | 0.75 | 4:1 |
| 5 | 4.25 | 4.75 | 0.875 | 0.15 | 6:1 |
| 6 | 4.25 | 4.75 | 3.5 | 0.6 | 6:1 |
| 7 | 4.25 | 4.75 | 5.25 | 0.875 | 6:1 |

The ingredients used to prepare the mucoadhesive layer for Formulations 2, 4 and 6 are summarized in the Table 2 below:

TABLE 2

Ingredients for preparing the mucoadhesive layer at pH 4.75

| | Amount (mg) | | |
|---|---|---|---|
| Ingredient | Formulation 2 3.11 cm² film | Formulation 4 3.11 cm² film | Formulation 6 3.58 cm² film |
| Purified Water | Constitutes 88.911% w/w of the wet blend | Constitutes 88.911% w/w of the wet blend | Constitutes 88.911% w/w of the wet blend |
| Propylene Glycol | 0.704 | 0.704 | 0.822 |
| Sodium Benzoate | 0.082 | 0.082 | 0.095 |
| Methylparaben | 0.137 | 0.137 | 0.160 |
| Propylparaben | 0.038 | 0.038 | 0.045 |
| Yellow Ferric Oxide | 0.082 | 0.082 | 0.095 |
| Citric Acid, Anhydrous | 0.082 | 0.082 | 0.096 |
| Vitamin E Acetate | 0.008 | 0.008 | 0.010 |
| Monobasic Sodium Phosphate, Anhydrous | 0.521 | 0.520 | 0.607 |
| Buprenorphine HCl | 3.234 | 3.234 | 3.773 |
| Polycarbophil | 0.980 | 0.979 | 1.143 |
| Hydroxypropyl Cellulose | 1.051 | 1.051 | 1.226 |
| Hydroxyethyl Cellulose | 3.144 | 3.143 | 3.668 |
| Carboxymethylcellulose Sodium | 8.399 | 8.398 | 9.799 |
| Sodium Hydroxide | 0.043 | 0.043 | 0.051 |

The mucoadhesive layer for Formulations 1 and 3 is prepared using the same ingredients as for formulations 2 and 4, respectively, except that the amounts of all ingredients are adjusted in direct proportion to the amount of buprenorphine and the film size of 0.78 cm². Similarly, the mucoadhesive layer for Formulations 5 and 7 are prepared using the same ingredients as for Formulation 6, except that the amounts of all ingredients are adjusted in direct proportion to the amount of buprenorphine and film size of 0.9 cm² for formulation 5 and 5.37 cm² for Formulation 7.

The ingredients used to prepare the backing layer in Formulation 2 are summarized in the Table 3 below:

TABLE 3

Ingredients for preparing the backing layer at pH 2.8 and 4.25

| | Amount (mg) | | |
|---|---|---|---|
| Ingredient | Formulation 2 3.11 cm² film | Formulation 4 3.11 cm² film | Formulation 6 3.58 cm² film |
| Purified Water | Constitutes 88.911% w/w of the wet blend | Constitutes 88.911% w/w of the wet blend | Constitutes 88.911% w/w of the wet blend |
| Hydroxypropyl Cellulose | — | 46.337 | 56.164 |
| Hydroxyethyl Cellulose | 65.182 | 22.920 | 27.740 |
| Sodium Benzoate | 0.296 | 0.371 | 0.449 |
| Methylparaben | 0.296 | 0.337 | 0.408 |
| Propylparaben | 0.074 | 0.067 | 0.082 |
| Dibasic Sodium Phosphate | — | 0.167 | 0.203 |
| Citric acid, anhydrous | 2.955 | 0.412 | 0.498 |
| Vitamin E acetate | 0.030 | 0.034 | 0.041 |
| Saccharin Sodium | 1.786 | 1.416 | 0.054 |
| Yellow Ferric Oxide | 0.057 | 0.044 | 1.751 |
| Triethyl Citrate | 3.774 | — | — |
| Citrus Flavor | — | 1.989 | 2.409 |
| Peppermint Oil | 0.608 | — | — |
| Naloxone HCl | 0.916 | 0.916 | 0.733 |

The backing layer for Formulations 1 and 3 is prepared using the same ingredients as for Formulations 2 and 4, respectively, except that the amounts of all ingredients are adjusted in direct proportion to the amount of naloxone and the film size of 0.78 cm². Similarly, the backing layer for Formulations 5 and 7 is prepared using the same ingredients as for Formulation 6, except that the amounts of all ingredients are adjusted in direct proportion to the amount of buprenorphine and film size of 0.9 cm² for Formulation 5 and 5.37 cm² for Formulation 7.

Example 2

Absorption Profiles for Formulations 1 and 2

This was an open label, active controlled study in healthy subjects in order to compare pharmacokinetic parameters of buprenorphine and naxolone from formulations 1 and 2 with Suboxone® sublingual tablets. Blood samples for analysis were collected pre-dose and at 0.5, 1, 1.5, 2, 3, 4, 6, 8, 12 and 16 hours post-dose and analyzed using the established procedures utilizing liquid chromatography and mass spectrometry (LC/MS). These selected pharmacokinetic parameters for buprenorphine and total naloxone are shown in Table 4.

TABLE 4

Selected Pharmacokinetic Parameters for Buprenorphine and Total Naloxone for low dose formulations.

| Pharmacokinetic Parameter | Formulation 1 (0.75 mg buprenorphine/0.1875 mg naloxone, backing layer at pH 2.8) | | Suboxone ® (2.0 mg buprenorphine/0.5 mg naloxone) | |
|---|---|---|---|---|
| | Buprenorphine | Total Naloxone | Buprenorphine | Total Naloxone |
| Mean $T_{max}$ (hr) | 2.29 | 1.29 | 1.75 | 0.92 |
| Mean $C_{max}$ (ng/mL) | 0.564 | 2.24 | 1.28 | 5.88 |
| Mean $AUC_{last}$ (hr * ng/mL) | 3.379 | 4.021 | 9.177 | 12.38 |
| Mean $AUC_{inf}$ (hr * ng/mL) | 3.868 | 4.585 | 10.92 | 13.26 |
| Mean $T_{1/2}$ | 10.72 | 2.58 | 23.72 | 4.15 |
| Absolute Bioavailability | 46% | — | 25% [1] | — |

[1] Roy, S. D. et al., Transdermal delivery of buprenorphine through cadaver skin (1994), *J. Pharm. Sci.*, 83: 126-130.

The results indicate that $C_{max}$ and $AUC_{inf}$ values for buprenorphine and total naloxone from Formulation 1 are less than the values observed from the control Suboxone® tablet.

Example 3

Absorption Profiles for Formulations 3 and 4

This study was designed to compare the plasma pharmacokinetic parameters of buprenorphine and naxolone from formulations 3 and 4 with Suboxone® sublingual tablets. This was a single dose, 2-period, crossover design with 24 subjects randomized to one of two, 12-subject groups. Each group received the device of the invention and Suboxone® tablets in random sequence, each separated by at least 5 days. Group 1 subjects received a single low dose Suboxone® tablet (containing 2.0 mg of buprenorphine and 0.5 mg of naloxone) and a single dose of formulation 3. Group 2 subjects received a single high dose Suboxone® tablet (containing 8.0 mg of buprenorphine and 2.0 mg of naloxone) and a single dose of formulation 4. Naltrexone was co-administered approximately 12 hours and 30 minutes prior to and approximately 12 and 24 hours after the single study drug doses. Serial blood samples for pharmacokinetic analyses were collected pre-dose and 15, 30, 45, 60, 75, 90, 105, 120, 135, 150, 165, 180, 210, 240, 270, 300, 330 and 360 minutes post-dose and at 8, 10, 12, 24 and 48 hours post-dose. Blood samples were analyzed using the established procedures utilizing liquid chromatography and mass spectrometry (LC/MS). The selected pharmacokinetic parameters for buprenorphine and free naloxone are shown in Tables 6 and 7.

TABLE 6

Selected Pharmacokinetic Parameters for Buprenorphine and Free Naloxone for low dose formulations

| Pharmacokinetic Parameter | Formulation 3 (0.75 mg buprenorphine/0.1875 mg naloxone, backing layer at pH 4.25) | | Suboxone ® (2.0 mg buprenorphine/0.5 mg naloxone) | |
|---|---|---|---|---|
| | Buprenorphine | Free Naloxone | Buprenorphine | Free Naloxone |
| Mean $T_{max}$ (hr) | 2.11 | 1.17 | 1.8 | 0.85 |
| Mean $C_{max}$ (ng/mL) | 1.10 | 0.0528 | 0.853 | 0.0441 |
| Mean $AUC_{last}$ (hr * ng/mL) | 5.325 | 0.1297 | 6.321 | 0.1151 |
| Mean $AUC_{inf}$ (hr * ng/mL) | 5.938 | 0.1346 | 7.339 | 0.1208 |
| Mean $T_{1/2}$ | 10.10 | 1.22 | 20.33 | 2.06 |
| Absolute Bioavailability | 75% | — | 25% | — |

TABLE 7

Selected Pharmacokinetic Parameters for Buprenorphine and Free Naloxone for high dose formulations

| Pharmacokinetic Parameter | Formulation 4 (3.0 mg buprenorphine/0.75 mg naloxone, backing layer at pH 4.25) | | Suboxone ® (8.0 mg buprenorphine/2.0 mg naloxone) | |
|---|---|---|---|---|
| | Buprenorphine | Free Naloxone | Buprenorphine | Free Naloxone |
| Mean $T_{max}$ (hr) | 2.17 | 1.05 | 1.70 | 0.92 |
| Mean $C_{max}$ (ng/mL) | 3.44 | 0.233 | 3.21 | 0.152 |
| Mean $AUC_{last}$ (hr * ng/mL) | 19.46 | 0.5815 | 23.05 | 0.4529 |
| Mean $AUC_{inf}$ (hr * ng/mL) | 21.50 | 0.5884 | 29.76 | 0.471 |

TABLE 7-continued

Selected Pharmacokinetic Parameters for Buprenorphine
and Free Naloxone for high dose formulations

|  | Formulation 4 (3.0 mg buprenorphine/0.75 mg naloxone, backing layer at pH 4.25) | | Suboxone ® (8.0 mg buprenorphine/2.0 mg naloxone) | |
|---|---|---|---|---|
| Pharmacokinetic Parameter | Buprenorphine | Free Naloxone | Buprenorphine | Free Naloxone |
| Mean $T_{1/2}$ | 18.82 | 2.80 | 29.21 | 6.33 |
| Absolute Bioavailability | 65% | — | 25% | — |

The results indicate that, unexpectedly, the absorption of buprenorphine from Formulations 3 and 4 are increased, as compared to control. This increase in buprenorphine absorption is particularly surprising in view of the results of Example 2 and is caused by the change of pH of the backing layer from 2.8 in Formulations 1 and 2 to 4.25 in Formulations 3 and 4.

The results also indicate that $C_{max}$ values for buprenorphine from Formulations 3 and 4 are comparable to values from the control Suboxone® tablets and that the $AUC_{inf}$ values for buprenorphine from the devices of the invention are slightly less than the values from the corresponding Suboxone® tablets. Further, the $C_{max}$ and $AUC_{inf}$ values for free (unconjugated) naloxone are greater than the values from the corresponding Suboxone® tablets.

Example 4

Absorption Profiles for Formulations 5, 6 and 7

This study was designed to assess the plasma pharmacokinetic parameters for buprenorphine and naloxone exposure following administration of Formulations 5, 6 and 7 comprising buprenorphine and naloxone present at the w/w ratio of 6:1 of buprenorphine to naloxone and with the backing layer formulated at pH of 4.25. This study was also designed to demonstrate the linearity of buprenorphine exposure across the range of doses. In addition, pharmacokinetic profiles following administration of four devices prepared according to formulation 5 (4×0.875/0.15 mg buprenorphine/naloxone) was compared with those from a single device prepared according to formulation 6 that contained an equivalent dose of actives (3.5/0.6 mg buprenorphine/naloxone).

This was an open label, single dose, 4-period crossover study in 20 healthy subjects. Each subject received 4 doses of buprenorphine in the devices of the invention in a random sequence, each dose separated by at least 7 days. The doses administered were 0.875/0.15 mg, 3.5/0.6 mg, 5.25/0.9 mg and 4×0.875/0.15 mg buprenorphine/naloxone in the devices prepared according to Formulations 5, 6, 7 and 5, respectively. Naltrexone was co-administered approximately 12 hours and 30 minutes prior to and approximately 12 and 24 hours after the single study drug doses. Serial blood samples for pharmacokinetic analyses were collected pre-dose and 15, 30, 45, 60, 75, 90, 105, 120, 135, 150, 165, 180, 210, 240, 270, 300, 330 and 360 minutes post-dose and at 8, 10, 12, 24 and 48 hours post-dose. Blood samples were analyzed using the established procedures utilizing liquid chromatography and mass spectrometry (LC/MS). The selected pharmacokinetic parameters for buprenorphine and free naloxone are shown in Tables 8 and 9.

TABLE 8

Selected Pharmacokinetic Parameters for Buprenorphine
and Free Naloxone for formulations 5 and 7

|  | Formulation 5 (0.875 mg buprenorphine/0.15 mg naloxone, backing layer at pH 4.25) | | Formulation 7 (5.25 mg buprenorphine/0.875 mg naloxone, backing layer at pH 4.25) | |
|---|---|---|---|---|
| Pharmacokinetic Parameter | Buprenorphine | Free Naloxone | Buprenorphine | Free Naloxone |
| Mean $T_{max}$ (hr) | 2.84 | 1.13 | 2.71 | 1.38 |
| Mean $C_{max}$ (ng/mL) | 1.15 | 0.0443 | 5.13 | 0.182 |
| Mean $AUC_{last}$ (hr * ng/mL) | 7.372 | 0.1166 | 33.28 | 0.4892 |
| Mean $AUC_{inf}$ (hr * ng/mL) | 8.380 | 0.1202 | 36.19 | 0.5233 |
| Absolute Bioavailability | ~60% | — | ~60% | — |

TABLE 9

Selected Pharmacokinetic Parameters for Buprenorphine and Free Naloxone
for formulation 6 and formulation 5 administered as 4 doses

| Pharmacokinetic Parameter | Formulation 6 (3.5 mg buprenorphine/0.6 mg naloxone, backing layer at pH 4.25) | | 4 x Formulation 5 (0.875 mg buprenorphine/0.15 mg naloxone, backing layer at pH 4.25) | |
|---|---|---|---|---|
| | Buprenorphine | Free Naloxone | Buprenorphine | Free Naloxone |
| Mean $T_{max}$ (hr) | 2.78 | 1.48 | 2.75 | 1.38 |
| Mean $C_{max}$ (ng/mL) | 4.03 | 0.179 | 3.89 | 0.182 |
| Mean $AUC_{last}$ (hr * ng/mL) | 24.77 | 0.4801 | 25.33 | 0.4892 |
| Mean $AUC_{inf}$ (hr * ng/mL) | 27.32 | 0.4883 | 27.29 | 0.5233 |
| Absolute Bioavailability | ~60% | — | — | — |

Figure 2:
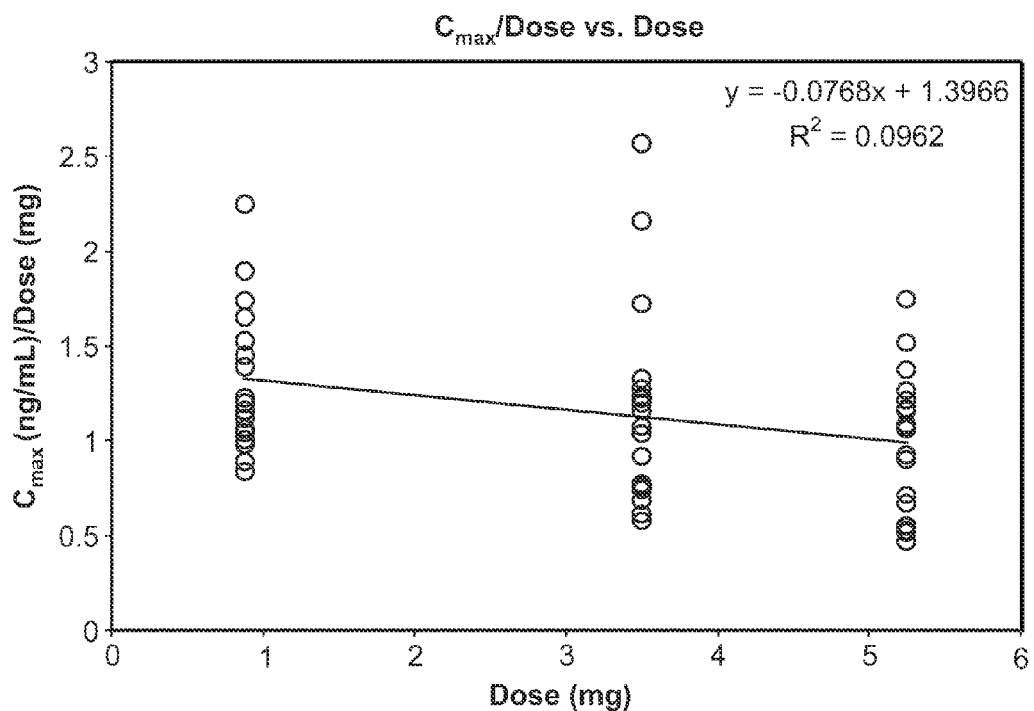
FIG. 2 is a graph showing assessment of dose-proportionality of buprenorphine $C_{max}$ after administration of the devices of the invention containing 0.875/0.15 mg, 3.5/0.6 mg and 5.25/0.9 mg of buprenorphine/naloxone as described in Example 4.
Figure 3:
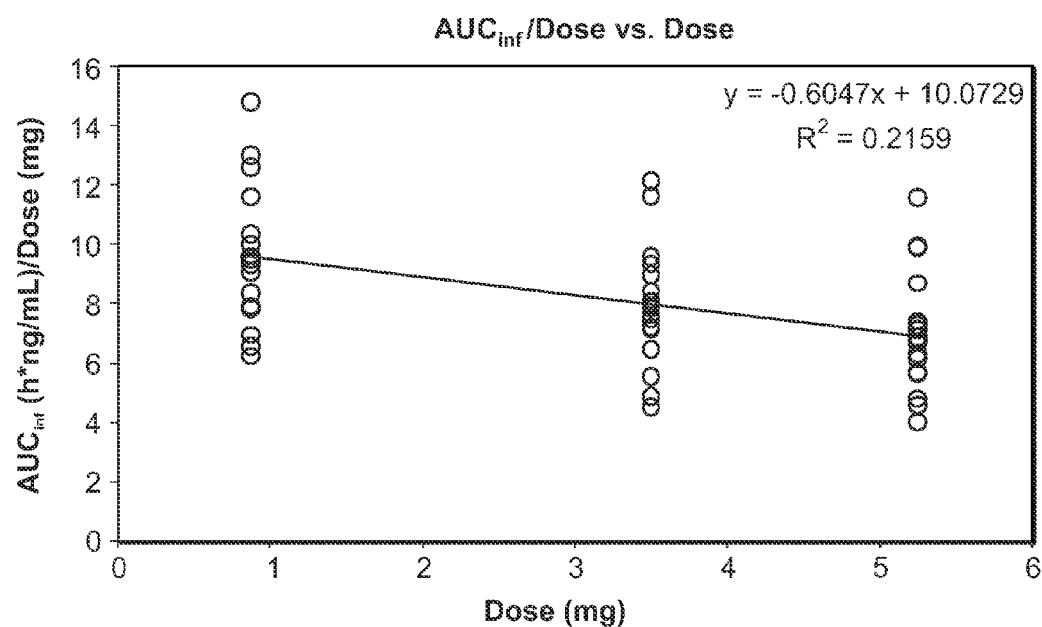
FIG. 3 is a graph showing assessment of dose-proportionality of buprenorphine $AUC_{inf}$ after administration of the devices of the invention containing 0.875/0.15 mg, 3.5/0.6 mg and 5.25/0.9 mg of buprenorphine/naloxone as described in Example 4.

The results of the study indicate that changing the w/w ratio of buprenorphine to naloxone from 4:1 to 6:1 results in decreased naloxone exposure that I s more in line with the exposure needed to precipitate withdrawal if abused but not so much as to precipitate the withdrawal if used as indicated. The results also indicate that $C_{max}$ and $AUC_{inf}$ of buprenorphine from formulations 5, 6 and 7 is dose proportional. Dose proportionality of buprenorphine $C_{max}$ and $AUC_{inf}$ are also illustrated by the graphs shown in FIGS. 2 and 3, respectively.

Example 5

Naloxone Withdrawal Study

The transmucosal devices of the invention that are prepared according to Formulations 1, 3 and 5 comprise relatively small doses of buprenorphine and naloxone (0.75 mg/0.19 mg and 0.875/0.15 mg buprenorphine/naloxone, as compared to 2 mg/0.5 mg buprenorphine/naloxone contained in the equivalent Suboxone® tablet). While the lower dose of the naloxone may be beneficial for the patient using the product correctly, it may not produce the expected aversive reaction experienced by those who are dependent on full-agonist opioids. Accordingly, the objective of the study was to determine the minimum effective dose of naloxone that will produce a withdrawal response when administered with a 0.75 mg dose of buprenorphine in opioid dependent subjects. The secondary objective of the study was to determine whether administration of a 0.75 mg dose of buprenorphine without naloxone will produce a withdrawal response in opioid dependent subjects.

Study Population

The study was designed to include a total of 12 adult subjects that completed the 4-period crossover. Subjects were eligible for inclusion in the study if all the following criteria applied:

subjects experienced chronic moderate to severe non-cancer pain that has been treated >100 mg morphine equivalents per day for at least 3 months prior to the study;

subjects displayed signs and symptoms of withdrawal (i.e., COWS score ≥5) following naloxone administration during the Naloxone Challenge.

Description of Study Medication

During the inpatient Treatment Visit subjects received a single, 3 mL IV bolus dose of each of the following treatments separated by at least 72 hours:

a) Buprenorphine 0.75 mg (B)
b) Buprenorphine 0.75 mg+naloxone 0.1 mg (BN1)
c) Buprenorphine 0.75 mg+naloxone 0.2 mg (BN2)
d) Placebo (5% dextrose) (P)

Study Procedures

Eligible subject exhibited signs of withdrawal, e.g., had a positive response (COWS≥5) to the Naloxone Withdrawal Test, following administration of up to eight 0.05 mg IV doses of naloxone.

Clinical Opiate Withdrawal Scale

The Clinical Opiate Withdrawal Scale (COWS) was used to evaluate symptoms of opioid withdrawal. The scale contains 11 items to rate signs and symptoms of opioid withdrawal including pulse rate, gastrointestinal upset, sweating, tremor, restlessness, yawning, pupil size, anxiety or irritability, bone or joint aches, gooseflesh skin, runny nose, tearing. Each symptom is rated on a unique scale. Total scores for the scale range from 0 to 48 with scores of 5-12 indicating mild withdrawal; scores of 13-24 indicating moderate withdrawal; scores of 25-36 indicating moderately severe withdrawal; and scores >36 indicating severe withdrawal.

Opioid Agonist Scale

Subjects were asked to evaluate the following items: nodding, heavy or sluggish feeling, dry mouth, carefree, good mood, energetic, turning of stomach, skin itchy, relaxed, coasting, soapbox, pleasant sick, drive, drunken, friendly, and nervous using a 5-point Likert scale (0=not at all, 1=a little, 2=moderately, 3=quite a bit, and 4=extremely).

Statistical Analysis

Descriptive statistics were used to summarize the results from the PD analyses at each timepoint for each treatment group, without formal statistical testing. A mixed effect model was fitted to the data for the change from baseline in total score where the model included factors for: the overall mean change; fixed effects due to sequence; treatment, time and period; and a random effect for subject nested within sequence. The least squares mean changes and standard errors were obtained and used to construct 95% CI for differences between treatments in a pair-wise fashion. Subject data collected after rescue time (i.e., time at which the subjects reaches COWS total score of 13 or more) were excluded to minimize the confounding effect of rescue on the PD analyses.

For COWS total score only, Time-to-Total score of ≥13 was calculated as time (hours) from first dose until the subject reports a total score of ≥13. Subjects who did not reach a total score of 13 or more were censored at 24 hours. This endpoint was summarized using the Kaplan-Meier method and 95% CI presented for median for each treatment arm.

Results

COWS Total-Score, and Rescue Results

Figure 4:
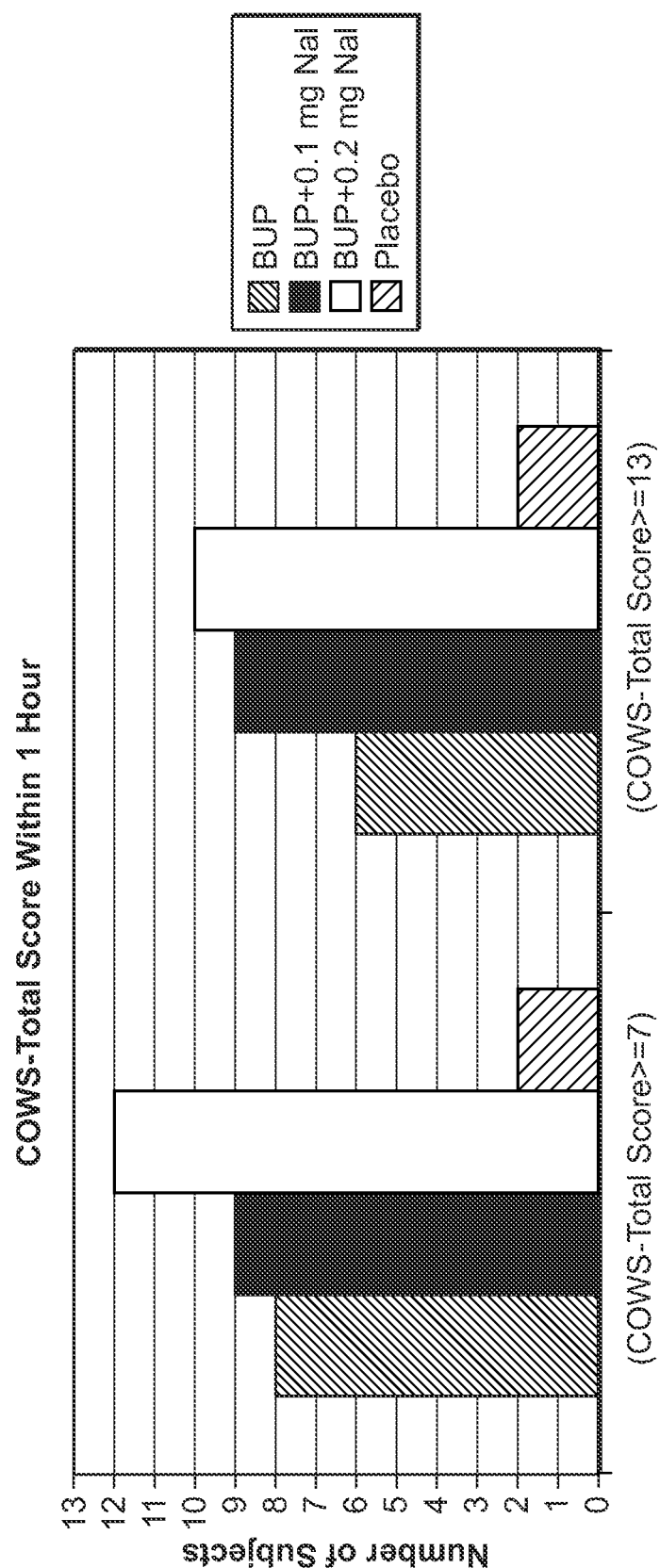
FIG. 4 is a graph showing COWS total scores recorded within 1 hour of subjects receiving study medication as a part of Naloxone Withdrawal Study as described in Example 5.
Figure 5:
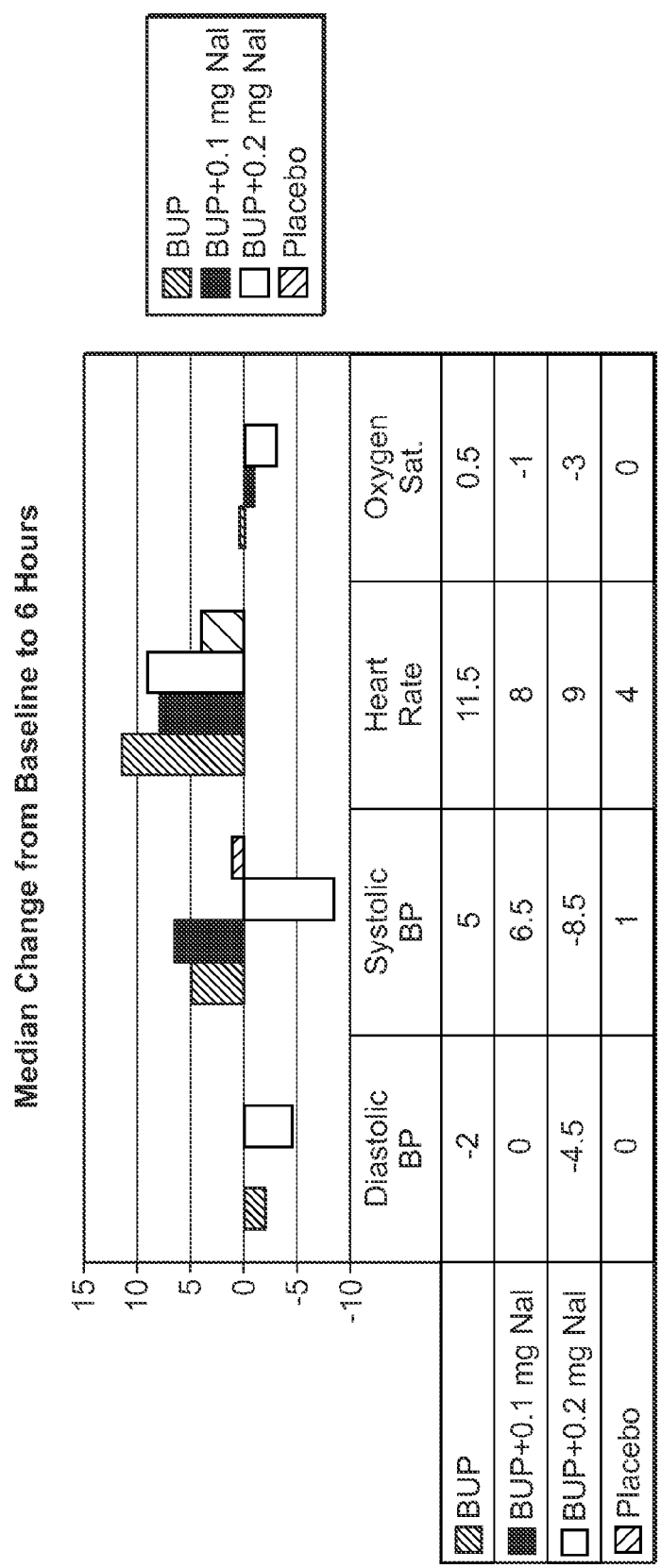
FIG. 5 is a graph showing changes in blood pressure, heart rate and oxygen saturation in subjects receiving study medication as a part of Naloxone Withdrawal Study as described in Example 5.

The number of subjects with COWS total score of at least 7 in the first hour post dose is shown on the left side of FIG. 4. Eight subjects on buprenorphine alone had a COWS value of at least 7 compared with 9 in the buprenorphine plus naloxone 0.1 mg group, 12 subjects in the buprenorphine plus naloxone 0.2 mg group, and two on placebo. Similarly, COWS≥13 were recorded for 6 buprenorphine subjects, 9 buprenorphine and naloxone 0.1 mg subjects, 10 buprenorphine and naloxone 0.2 mg, and 2 placebo patients. Two of the 15 subjects experienced withdrawal on each of the study treatments, including placebo.

In the buprenorphine alone group, 7(47%) of the 15 subjects experienced moderate withdrawal with COWS score of at least 13, and all 7 were rescued. In the 8 subjects that did not receive rescue, the median COWS at 1 hour post dose was 1.

In the buprenorphine plus 0.1 mg of naloxone group, 9 subjects (60%) had COWS≥13 and all 9, plus an additional subject that was rescued. In the 5 subjects that did not receive rescue, the median COWS at one hour post dose was 0.

In the buprenorphine plus 0.2 mg of naloxone group, 11 subjects (73%) had COWS scores of at least 13 and each of these received rescue. In the 4 subjects that were not rescued, the median COWS at one hour post dose was 3.

TABLE 10

Summary of COWS Total Scores and Rescue Results

| Parameter | B (n = 15) | BN1 (n = 15) | BN2 (n = 15) | P (n = 15) |
|---|---|---|---|---|
| COWS >= 13, n (%) | 7 (47%) | 9 (60%) | 11 (73%) | 2 (1%) |
| Rescued n (%) | 7 (47%) | 10 (67%) | 11 (73%) | 2 (1%) |
| Median COWS at One Hour Post Dose | 1 | 0 | 3 | 0 |

Drug Effect Questionnaire (DEQ)—Observed Median Values 1 Hour Post Dose

Median DEQ responses at one hour in those subjects that were not rescued are shown in Table 6 below.

The median DEQ scores for each parameter in all but the BN2 group were zero or nearly zero at one hour post dose. In contrast, the BN2 group had significantly higher scores on drug effect, nausea, bad effect, dizziness, and feeling sick.

The median score for good effect and how high are you was zero at one hour in all treatment groups.

TABLE 11

Median DEQ responces at one hour in subjects who were not rescued.

| Parameter | B (n = 15) | BN1 (n = 15) | BN2 (n = 15) | P (n = 15) |
|---|---|---|---|---|
| Drug effect | 2 | 0 | 49 | 0 |
| Nausea | 0 | 0 | 38 | 0 |
| Like drug | 0 | 0 | 0 | 0 |
| Good effect | 0 | 0 | 0 | 0 |
| Bad Effect | 0 | 0 | 27 | 0 |
| Dizzy | 0 | 0 | 14 | 0 |
| Feel Sleepy | 0 | 0 | 0 | 0 |
| Feel sick | 0 | 0 | 30 | 0 |
| How high are you | 0 | 0 | 0 | 0 |

The results of this double-blind, placebo controlled study in opioid dependent subjects indicate that intravenous buprenorphine doses of 0.75 mg have little abuse potential, and that the addition of naloxone increases both the incidence of withdrawal as well as negative drug evaluations. Thus, naloxone at doses of 0.1 and 0.2 mg, provide an abuse deterrent effect to a 0.75 mg dose of buprenorphine when administered intravenously to opioid dependent subjects.

EQUIVALENTS

While the present invention has been described in conjunction with various embodiments and examples it is not intended that the present teachings be limited to such embodiments or examples. On the contrary, the present invention encompasses various alternatives, modifications, and equivalents, as will be appreciated by those of skill in the art.

The invention claimed is:

1. An abuse deterrent mucoadhesive device for use in managing pain or opioid dependence, the device comprising:
   a mucoadhesive layer comprising between about 0.075 and about 12 mg of buprenorphine buffered to a pH of between about 4.0 and about 6.0; and
   a backing layer comprising between about 0.0125 and about 2 mg of naloxone buffered to a pH between about 4.0 and about 4.8,
   wherein the pH of the mucoadhesive layer and the pH of the backing layer are different,
   wherein the mucoadhesive layer and the backing layer comprise different combinations of polymers but each layer comprises at least one water-erodible polymer selected from the group consisting of: cellulosic polymers, olefinic polymers, polyethers and polyalcohols, and
   wherein following transmucosal administration excessive exposure to buprenorphine is avoided while the abuse-deterrent effect of naloxone is retained.

2. The device according to claim 1, wherein the w/w ratio of buprenorphine to naloxone present in the device is between 1:1 and 10:1.

3. The device according to claim 2, wherein the w/w ratio of buprenorphine to naloxone present in the device is 6:1.

4. The device according to claim 3, wherein the mucoadhesive layer is buffered to a pH of between about 4.50 and about 5.50 and the wherein the backing layer is buffered to a pH of between about 4.10 and about 4.4.

5. The device according to claim 4, wherein the mucoadhesive layer is buffered to a pH of about 4.75 and the backing layer is buffered to a pH of about 4.25.

6. The device according to claim 1 wherein the bioavailability of buprenorphine absorbed from the device is greater than 40%.

7. The device according to claim 1, wherein the at least one water-erodible polymer is selected from the group consisting of: polyacrylic acid (PAA), sodium carboxymethyl cellulose (NaCMC), hydroxypropylmethyl cellulose (HPMC), polyvinylpyrrolidone (PVP), hydroxyethylmethyl cellulose (HEMC), hydroxyethyl cellulose (HEC), hydroxypropyl cellulose (HPC), polyvinyl alcohol (PVA), polyethylene glycol (PEG), polyethylene oxide (PEO), and ethylene oxide-propylene oxide co-polymers.

* * * * *